United States Patent
Hanawa

(10) Patent No.: US 9,891,263 B2
(45) Date of Patent: Feb. 13, 2018

(54) PARTIAL DISCHARGE MEASUREMENT METHOD, PARTIAL DISCHARGE MEASUREMENT DEVICE, AND METHOD OF PRODUCING INSULATED WIRE

(71) Applicant: HITACHI METALS, LTD., Tokyo (JP)

(72) Inventor: Hidehito Hanawa, Tokyo (JP)

(73) Assignee: HITACHI METALS, LTD., Tokyo (JP)

( * ) Notice: Subject to any disclaimer, the term of this patent is extended or adjusted under 35 U.S.C. 154(b) by 78 days.

(21) Appl. No.: 15/055,325

(22) Filed: Feb. 26, 2016

(65) Prior Publication Data

US 2016/0282403 A1  Sep. 29, 2016

(30) Foreign Application Priority Data

Mar. 23, 2015 (JP) .................................. 2015-060171

(51) Int. Cl.
*H01H 31/12* (2006.01)
*G01R 31/14* (2006.01)
*G01R 1/00* (2006.01)
*G01N 1/00* (2006.01)

(52) U.S. Cl.
CPC ................ *G01R 31/14* (2013.01); *G01N 1/00* (2013.01); *G01N 2201/00* (2013.01); *G01R 1/00* (2013.01)

(58) Field of Classification Search
CPC ......... G01R 1/00; G01N 1/00; G01N 2201/00
See application file for complete search history.

(56) References Cited

U.S. PATENT DOCUMENTS

| | | | | |
|---|---|---|---|---|
| 3,005,150 | A * | 10/1961 | Behr | G01R 31/12 324/541 |
| 4,417,701 | A * | 11/1983 | Moritz | G01N 27/205 242/431 |
| 5,530,364 | A * | 6/1996 | Mashikian | G01R 31/083 324/242 |
| 5,760,590 | A * | 6/1998 | Striffler | G01R 31/022 324/513 |
| 6,184,691 | B1 * | 2/2001 | Prough | G01R 31/1263 324/515 |

(Continued)

FOREIGN PATENT DOCUMENTS

JP  2008-082904 A  4/2008

*Primary Examiner* — Jermele M Hollington
*Assistant Examiner* — Temilade Rhodes-Vivour
(74) *Attorney, Agent, or Firm* — McGinn I.P. Law Group, PLLC.

(57) ABSTRACT

A partial discharge measurement method includes: a moving step of moving an insulated wire including an insulating layer on a surface of the insulated wire; a voltage applying step of bringing an electrode which is connected to a power supply into contact with the insulating layer of the insulated wire which is moving, and applying a predetermined test voltage to the insulating layer while moving the insulated wire; a detection step of detecting, as a partial discharge signal, a signal which is more than or equal to a threshold value among signals involved in partial discharge events occurring from the insulating layer due to application of the predetermined test voltage; and a determination step of determining, based on a result in the detection step, frequency of occurrence of partial discharge events at the predetermined test voltage.

9 Claims, 2 Drawing Sheets

(56) References Cited

U.S. PATENT DOCUMENTS

| | | | |
|---|---|---|---|
| 6,313,640 B1 * | 11/2001 | Nasrallah | G01R 31/1272 324/522 |
| 2011/0248721 A1 * | 10/2011 | Higgins | G01R 31/1272 324/537 |

* cited by examiner

PARTIAL DISCHARGE MEASUREMENT METHOD, PARTIAL DISCHARGE MEASUREMENT DEVICE, AND METHOD OF PRODUCING INSULATED WIRE

The present application is based on Japanese patent application No. 2015-060171 filed on Mar. 23, 2015, the entire contents of which are incorporated herein by reference.

BACKGROUND OF THE INVENTION

1. Field of the Invention

The present invention relates to a partial discharge measurement method, a partial discharge measurement device, and a method of producing an insulated wire.

2. Description of the Related Art

An insulated wire includes an insulating layer so as to cover an outer periphery of a conductor. In the insulated wire, the application of a high voltage to the conductor generates an electric field around the insulating layer, and an increase in the electric field strength causes a partial discharge event from the insulating layer. The occurrence of the partial discharge event causes the insulating layer to deteriorate, and may finally result in a dielectric breakdown.

Thus, in order to prevent a dielectric breakdown due to a partial discharge event when an insulated wire is used in an electrical device or the like, it is necessary to ascertain in advance what level of an applied voltage causes a partial discharge event, that is, the level of a voltage at which a partial discharge event begins to occur, which is called "partial discharge inception voltage" (hereinafter also referred to as PDIV). In particular, in recent years, in an electrical device, such as a motor, inverter control has been performed from the viewpoint of high efficiency, the occurrence of a surge voltage has resulted in the application of a high voltage to an insulated wire constituting the motor or the like, and thus it has become increasingly important to ascertain a PDIV of an insulating layer.

An example of a method of measuring a PDIV is a method in which part of a produced insulated wire is extracted as a sample, a voltage is applied between the terminals thereof, and the occurrence or nonoccurrence of a partial discharge event due to the application of voltage is measured by using an optical sensor (generally, a photomultiplier, an electromagnetic-wave sensor, or the like), a quantity of charge discharged, a current value, and so forth (see, for example, Japanese Unexamined Patent Application Publication No. 2008-82904).

SUMMARY OF THE INVENTION

In the existing method of measuring a PDIV, however, since part of a produced insulated wire is extracted as a sample and a PDIV of the sample is measured, there is a problem in that the measured PDIV is not a value guaranteed for the entire length of the insulated wire but a value obtained in the part of the insulated wire.

Specifically, in some insulated wires, the thickness of an insulating layer varies along the length of the insulating layer. When a PDIV of such an insulating layer is measured, a value measured in a thick portion is relatively high, and a value measured in a thin portion is relatively low. If a high value measured in the thick portion is regarded as a PDIV of an entire insulated wire, when a voltage close to the PDIV is applied to the insulated wire, a partial discharge event may occur in a portion being relatively thin in thickness. For this reason, a minimum value measured in a portion being thinnest in thickness in the entire insulated wire has to be ascertained as a PDIV. In the case where a voltage lower than the minimum value of the PDIV is applied, the minimum value can be a guaranteed value which ensures that a partial discharge event can be prevented over the entire length of the insulated wire. In this regard, in the case where part of the insulated wire is extracted as a sample and a PDIV thereof is measured as in the related art, a measurement is not necessarily made in a portion being thinnest in thickness, and thus the measured value is inadequate as a guaranteed value of the PDIV.

The present invention has been made in view of the above-described problem, and an object thereof is to provide a technique which enables a partial discharge event in an insulating layer to be measured over the entire length of an insulated wire.

(1) According to one exemplary aspect of the invention, a partial discharge measurement method includes: a moving step of moving an insulated wire including an insulating layer on a surface of the insulated wire; a voltage applying step of bringing an electrode which is connected to a power supply into contact with the insulating layer of the insulated wire which is moving, and applying a predetermined test voltage to the insulating layer while moving the insulated wire; a detection step of detecting, as a partial discharge signal, a signal which is more than or equal to a threshold value among signals involved in partial discharge events occurring from the insulating layer due to application of the predetermined test voltage; and a determination step of determining, based on a result in the detection step, frequency of occurrence of partial discharge events at the predetermined test voltage.

(2) According to another exemplary aspect of the invention, the method includes performing the partial discharge measurement method in an in-line manner after an insulating layer forming step of forming an insulating layer on an outer periphery of a conductor.

(3) According to another exemplary aspect of the invention, the partial discharge measurement device includes: a moving unit which moves an insulated wire including an insulating layer on a surface of the insulated wire; an electrode which is connected to a power supply generating a predetermined test voltage, is disposed so as to come into contact with the insulating layer of the insulated wire which is moving, and applies the predetermined test voltage to the insulating layer; a detection unit which detects, as a partial discharge signal, a signal which is more than or equal to a threshold value among signals involved in partial discharge events occurring from the insulating layer due to application of the predetermined test voltage; and a determination unit which determines, based on a result in the detection unit, frequency of occurrence of partial discharge events at the predetermined test voltage.

The present invention enables a partial discharge event in the insulating layer to be measured over the entire length of the insulated wire.

BRIEF DESCRIPTION OF THE DRAWINGS

The foregoing and other exemplary purposes, aspects and advantages will be better understood from the following detailed description of the invention with reference to the drawings, in which.

DESCRIPTION OF THE PREFERRED EMBODIMENT

As described above, in the existing method of measuring a PDIV, a part cut from an insulated wire is measured as a sample. For example, first, a voltage having a frequency of 50 Hz is applied to this sample while being increased. Subsequently, a partial discharge event occurs from an insulating layer of the sample due to the application of the voltage. Among such partial discharge events, the number of times a partial discharge event in which a quantity of charge discharged is more than or equal to 100 pC has occurred is measured. Then, a voltage at which the number of times the partial discharge event has occurred is more than or equal to 50 per second is measured as a PDIV. Although this method enables measurement of a PDIV of the insulating layer, since the PDIV is a value measured in the part of the insulated wire, the reliability of the value is low for a guaranteed value covering the entire length of the insulated wire.

The inventor has conducted an investigation on the above-described problem, and thereby found that, if, while an insulated wire is being moved at a fixed speed, a voltage is applied to an insulating layer and a partial discharge event occurring in the insulating layer is measured, a partial discharge event can be measured over the entire length of the insulated wire, and a guaranteed value of a PDIV of the insulated wire is obtained.

Furthermore, in order to apply a voltage to the insulating layer of the moving insulated wire under the same condition as that in the existing method, it has been found that a time period of contact between the insulating layer of the moving insulated wire and an electrode, a frequency of a voltage to be applied, and so forth have to be appropriately set so that a predetermined relationship is satisfied.

The present invention has been accomplished on the basis of the findings.

Figure 1:
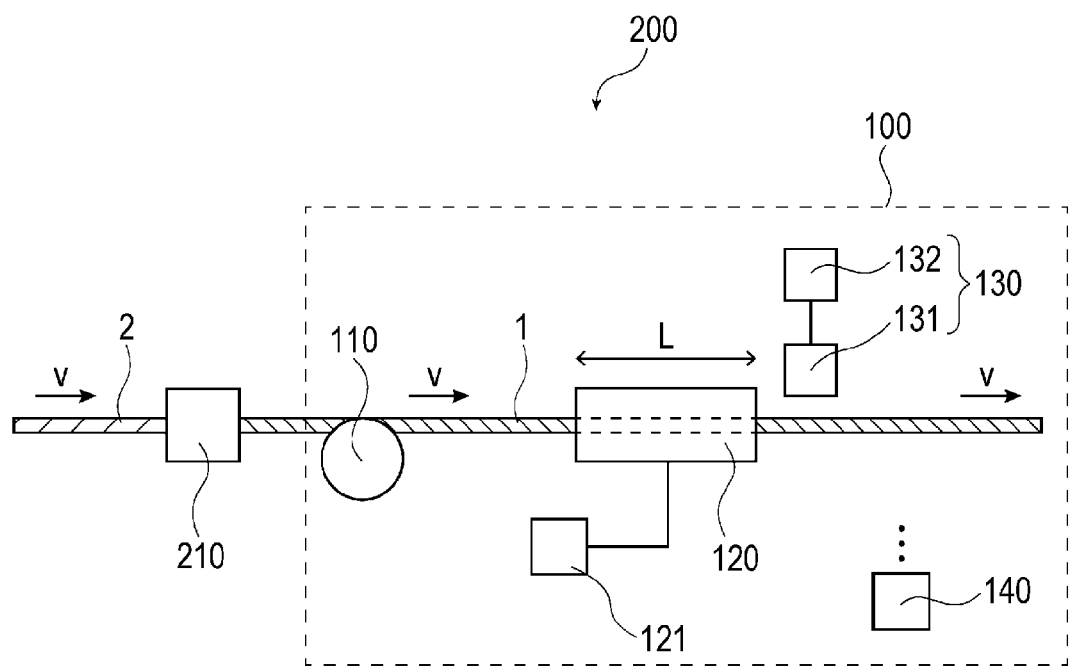
FIG. 1 is a schematic view of an insulated wire production apparatus into which a partial discharge measurement device according to an embodiment of the present invention is incorporated.
Figure 2:
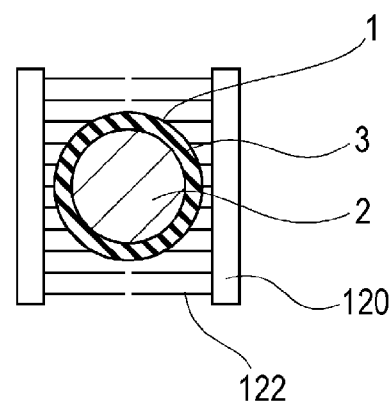
FIG. 2 illustrates contact between an insulated wire which is substantially circular in cross section and an electrode.
Figure 3:
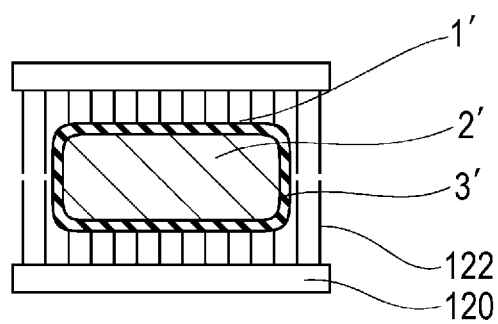
FIG. 3 illustrates contact between an insulated wire which is substantially rectangular in cross section and the electrode.

An embodiment of the present invention will be described below with reference to the drawings. FIG. 1 is a schematic view of an insulated wire production apparatus into which a partial discharge measurement device according to an embodiment of the present invention is incorporated. FIG. 2 illustrates contact between an insulated wire which is substantially circular in cross section and an electrode. FIG. 3 illustrates contact between an insulated wire which is substantially rectangular in cross section and the electrode.

<Object to be Measured>

First, before a partial discharge measurement device is described, an insulated wire to be measured will be described.

For example, as illustrated in FIG. 2, an insulated wire 1 includes a conductor 2 which is substantially circular in cross section, and an insulating layer 3 provided so as to cover an outer periphery of the conductor 2.

Examples of the conductor 2 which can be used include an aluminum wire, a silver wire, and a nickel wire in addition to metal wires typically used, such as a copper wire and a copper alloy wire. Additionally, a metal wire whose outer periphery is plated with metal, such as nickel, may be used. Furthermore, a bunch stranded conductor produced by stranding metal wires can be used. It is noted that the cross-section shape of the conductor 2 is not limited to a circle, and may be a substantially rectangular shape (flat rectangular shape). For example, as illustrated in FIG. 3, a conductor 2' which is substantially rectangular in cross section can also be used.

The insulating layer 3 is formed using an insulating coating (which is called "enamel coating") containing, for example, a polyester imide, polyamide imide, polyimide, or the like. The thickness of the insulating layer 3 ranges from 30 μm to 150 μm inclusive, for example.

<Insulated Wire Production Apparatus>

Next, an insulated wire production apparatus into which a partial discharge measurement device according to the embodiment of the present invention is incorporated will be described.

As illustrated in FIG. 1, an insulated wire production apparatus 200 includes an insulating layer forming device 210 which forms the insulating layer 3 on the outer periphery of the conductor 2 being conveyed to produce the insulated wire 1, and a partial discharge measurement device 100 which measures a partial discharge event in the produced insulated wire 1.

<Partial Discharge Measurement Device>

The partial discharge measurement device 100 moves the insulated wire 1 including the insulating layer 3 formed on the surface of the insulated wire 1, simultaneously applies a test voltage and detects a partial discharge event occurring, and thus measures the frequency of occurrence of partial discharge events over the entire length of the insulated wire 1. As illustrated in FIG. 1, the partial discharge measurement device 100 includes a moving unit 110, an electrode 120, a detection unit 130, and a determination unit 140.

The moving unit 110 feeds the insulated wire 1 and moves it at a predetermined speed along its length.

The electrode 120 is provided on a path through which the fed insulated wire 1 moves, and is disposed so as to come into contact with the surface (insulating layer 3) of the insulated wire 1. The electrode 120 is connected to a power supply 121 generating a predetermined test voltage, and applies the predetermined test voltage to the insulating layer 3 of the insulated wire 1 which passes through the electrode 120. A test voltage is preferably an alternating-current (AC) voltage, and, for example, a sinusoidal voltage which periodically varies can be used.

As illustrated in FIG. 1, when the insulating layer 3 of the moving insulated wire 1 comes into contact with the electrode 120, the electrode 120 applies an AC voltage serving as a test voltage to a contact area of the insulating layer 3 with the electrode 120. That is, the AC voltage is applied to a predetermined area of the insulating layer 3 until the area has passed through the electrode 120 from when the area came into contact with the electrode 120. On this occasion, assuming that a speed at which the insulated wire 1 is moved is v m/min and the length of the electrode 120 is L mm, a time period until the predetermined area of the insulating layer 3 has passed through the electrode 120 from when it came into contact with the electrode 120, that is, a time period during which the predetermined area of the insulating layer 3 is in contact with the electrode 120 is L/1000 v min, that is, 60 L/1000 v s. Assuming that a frequency of the AC voltage is f Hz, the AC voltage is applied to the predetermined area of the insulating layer 3 by the amount of the number of periods T represented by the following general equation (1) while the predetermined area is in contact with the electrode 120. In this way, the electrode 120 having the length L applies an AC voltage of the frequency f to the insulating layer 3 of the insulated wire 1 moving at the speed v, and thus can apply the AC voltage to the insulating layer 3 uniformly along its length by the amount of the number of periods T.

$$T = \frac{60 \, L}{1000 \, v} f \qquad (1)$$

The electrode 120 may be any electrode capable of applying a test voltage to the insulating layer 3 of the moving insulated wire 1 uniformly. In order that the insulating layer 3 which comes into contact with the electrode 120 does not become damaged, the electrode 120 preferably includes a flexible conductive brush 122 which is made of, for example, carbon and is provided on a surface side which comes into contact with the insulating layer 3 as illustrated in FIG. 2.

It is noted that the length L of the electrode 120 denotes a length along a direction in which the insulated wire 1 moves in the electrode 120.

The detection unit 130 is provided along the path through which the insulated wire 1 moves, and is disposed in the proximity of the electrode 120 so as to be able to detect a partial discharge event occurring from the insulating layer 3. The detection unit 130 detects, as a partial discharge signal, a signal which is more than or equal to a threshold value among signals involved in partial discharge events occurring in the insulating layer 3 due to the application of the test voltage. For example, the detection unit 130 includes a sensor unit 131 which captures a signal involved in a partial discharge event, and a partial discharge monitor unit 132 which is connected to the sensor unit 131 and detects, as a partial discharge signal, a signal which is more than or equal to the threshold value among signals captured by the sensor unit 131.

The sensor unit 131 captures, as a signal involved in a partial discharge event, discharge light or an electromagnetic wave caused by the partial discharge event, and converts it into a quantity of charge discharged responsive to its intensity. Although the sensor unit 131 may be any unit capable of detecting a partial discharge event occurring in the moving insulated wire 1, a luminescence sensor or the like is preferably used. As the luminescence sensor, for example, a photomultiplier, an electromagnetic-wave sensor (patch antenna), or the like can be used.

The partial discharge monitor unit 132 is connected to the sensor unit 131, and detects, as a partial discharge signal, a signal which is more than or equal to the threshold value among signals captured by the sensor unit 131. Among signals captured by the sensor unit 131, there may be, for example, a signal coming from the outside other than signals resulting from partial discharge events. For this reason, the partial discharge monitor unit 132 detects, as a partial discharge signal resulting from a partial discharge event, a signal which is more than or equal to the threshold value among signals involved in partial discharge events. For example, the partial discharge monitor unit 132 detects, as a partial discharge event, discharge light whose quantity of charge discharged is more than or equal to 100 pC. Then, the partial discharge monitor unit 132 measures the detection number of times N a partial discharge signal has been detected.

The determination unit 140 determines, on the basis of a result in the detection unit 130, the frequency of occurrence of partial discharge events occurring when the predetermined test voltage is applied to the insulating layer 3. For example, the determination unit 140 refers to the detection number of times N a partial discharge signal has been detected by the detection unit 130, and determines that the frequency of occurrence of partial discharge events at the test voltage increases as the detection number of times N increases.

From the viewpoint of an accurate determination of the frequency of occurrence of partial discharge events, it is preferable that the determination unit 140 refers to the number of periods T of an AC voltage applied to the insulating layer 3 by the electrode 120 and the detection number of times N a partial discharge signal has been detected by the detection unit 130, and determines that the frequency of occurrence of partial discharge events is high when the relationship of T≤N is satisfied. In the case of T≤N, the partial discharge signal has been detected one or more times per period of the applied AC voltage, thus representing that the frequency of occurrence of partial discharge events is high. In the case where the frequency of occurrence of partial discharge events is high, a dielectric breakdown is likely to occur in the insulating layer 3 when the predetermined test voltage is applied, and thus it is determined in a comprehensive manner that partial discharge events have occurred. On the other hand, in the case of T>N, the frequency of occurrence of partial discharge events is low, a dielectric breakdown is not likely to occur in the insulating layer 3 even if a partial discharge event occurs, and thus it is determined in a comprehensive manner that no partial discharge events have occurred.

In the partial discharge measurement device 100 according to the embodiment, it is preferable that the length L of the electrode 120, the speed v at which the moving unit 110 moves the insulated wire 1, and the frequency f of an AC voltage are adjusted so that the number of periods T represented by the above-described equation (1) is more than or equal to 50. This enables the same accuracy of measurement as that in the case where a partially-cut sample is measured without the insulated wire 1 being moved to be obtained. That is, in the case where a measurement is made without the insulated wire 1 being moved, an AC voltage having a frequency of 50 Hz is applied to the cut sample, and thus the AC voltage is applied to the sample by the amount of 50 periods. In this regard, in the embodiment, the number of periods T can be set to 50 or more by adjusting the length L of the electrode 120, the speed v, and the frequency f, thereby enabling the same accuracy of measurement as that in the case where a measurement is made without the insulated wire 1 being moved to be obtained.

The length L of the electrode 120 is not limited to a particular length, but preferably ranges from 25 mm to 200 mm inclusive. When the length L of the electrode 120 is more than or equal to 25 mm, a sufficient time period of contact of the insulating layer 3 with the electrode 120 can be secured, thereby enabling accurate measurement of a partial discharge event. On the other hand, when the length L of the electrode 120 is less than or equal to 200 mm, a device size can be reduced.

The speed v at which the moving unit 110 moves the insulated wire 1 is not limited to a particular speed, but preferably ranges from 5 m/min to 40 m/min inclusive. When the insulated wire 1 is moved quickly at the speed v of 5 m/min or more, a time period in which a partial discharge event is measured over the entire length of the insulated wire 1 is reduced, thereby enabling an increase in measurement efficiency. On the other hand, when the speed v is less than or equal to 40 m/min, a sufficient time period of contact of the insulating layer 3 with the electrode 120 can be secured, thereby enabling accurate measurement of a partial discharge event.

The frequency f of an AC voltage generated as a test voltage by the power supply 121 is not limited to a particular frequency, but preferably ranges from 10 Hz to 1000 Hz inclusive. When the frequency f ranges from 10 Hz to 1000 Hz inclusive, the number of periods T can be increased, thereby enabling accurate measurement of a partial discharge event.

<Partial Discharge Measurement Method>

Next, a partial discharge measurement method using the above-described partial discharge measurement device 100 will be described.

A partial discharge measurement method according to the embodiment includes a moving step, a voltage applying step, a detection step, and a determination step.

First, the moving unit 110 moves the insulated wire 1 at a predetermined speed v m/min.

Subsequently, the insulated wire 1 is pulled into the electrode 120, and the electrode 120 having a length L mm is brought into contact with the insulating layer 3. Specifically, as illustrated in FIG. 2, a pair of electrodes 120 each including the conductive brush 122 provided on one surface is disposed so that the electrodes face each other and surround the outer periphery of the insulated wire 1 with the conductive brush 122, the insulated wire 1 is inserted between the pair of the electrodes 120, and the pair of electrodes 120 is brought into contact with the insulating layer 3. Then, as a test voltage, an AC voltage having a maximum value $V_0$ Vp and a frequency f Hz is applied to the insulating layer 3 from the power supply 121 via the pair of electrodes 120. Thus, the AC voltage is applied to the insulating layer 3 of the moving insulated wire 1 uniformly by the amount of the number of periods T represented by the following equation (1).

$$T = \frac{60}{1000} \frac{L}{v} f \quad (1)$$

Subsequently, the sensor unit 131 of the detection unit 130 captures a signal involved in a partial discharge event occurring from the insulating layer 3 due to the application of the test voltage. Then, the partial discharge monitor unit 132 of the detection unit 130 detects, as a partial discharge signal, a signal which is more than or equal to a threshold value among signals captured by the sensor unit 131. Specifically, the partial discharge monitor unit 132 detects, as a partial discharge event, discharge light whose quantity of charge discharged is more than or equal to 100 pC. Then, the partial discharge monitor unit 132 measures the detection number of times N the partial discharge event has been detected. In the embodiment, while the insulated wire 1 is being moved, a partial discharge signal is detected and the detection number of times N the partial discharge signal has been detected is measured. Thus, the detection number of times N in the insulating layer 3 is measured over the entire length of the insulated wire 1.

Subsequently, the determination unit 140 determines, on the basis of a result in the detection unit 130, the frequency of occurrence of partial discharge events occurring when the predetermined test voltage is applied to the insulating layer 3. In this determination, the number of periods T of the AC voltage applied to the insulating layer 3 in the above-described voltage applying step and the detection number of times N the partial discharge signal has been detected in the detection step are referred to, and it is determined that the frequency of occurrence of partial discharge events is high when the relationship of T≤N is satisfied. Thus, it is determined in a comprehensive manner that partial discharge events have occurred. This determination is made while the insulated wire 1 is being moved, and thus the frequency of occurrence of partial discharge events is determined over the entire length of the insulated wire 1.

When a test voltage having the maximum value $V_0$ is applied, if the frequency of occurrence of partial discharge events is low over the entire length of the insulated wire 1 in this determination, it can be ensured that a partial discharge event is not likely to occur even if a voltage $V_0$ is applied to this insulated wire 1, and that a dielectric breakdown is not likely to occur. That is, this voltage $V_0$ can be a guaranteed value of a PDIV of the insulated wire 1.

On the other hand, when the test voltage having the maximum value $V_0$ is applied, if there is a portion in which the frequency of occurrence of partial discharge events is high in the insulated wire 1, the guaranteed value of the PDIV of the insulated wire 1 is found to be lower than the voltage $V_0$. In this case, for example, the maximum value of the test voltage is gradually reduced from $V_0$ and a measurement is made. Then, a maximum value $V_1$ at which the frequency of occurrence of partial discharge events is low over the entire length of the insulated wire 1 is obtained, and may be set as the guaranteed value.

Furthermore, in the above-described determination, from the detection number of times N the partial discharge signal has been detected which has been measured over the entire length of the insulated wire 1, a portion in which the measured detection number of times N is large (a portion in which the frequency of occurrence of partial discharge events is high) is found to be thinner in the thickness of the insulating layer 3 than a portion in which the measured detection number of times N is small (a portion in which the frequency of occurrence of partial discharge events is low). Then, the thickness in a portion in which the detection number of times N is largest can be regarded as a minimum thickness in the insulated wire 1. Thus, the frequency of occurrence of partial discharge events is determined over the entire length of the insulated wire 1, thereby enabling a minimum value of the thickness of the insulating layer 3 of the insulated wire 1 to be ascertained.

<Method of Producing Insulated Wire>

Next, a method of producing the insulated wire 1 will be described in which the above-described partial discharge measurement method is performed in an in-line manner after an insulating layer forming step of forming the insulating layer 3 on the outer periphery of the conductor 2. The term "in-line" here denotes that the partial discharge measurement method is performed in a step of producing the insulated wire 1. That is, the insulating layer 3 is formed on the outer periphery of the conductor 2 so that the insulated wire 1 is produced, and simultaneously the produced insulated wire 1 is continuously subjected to a partial discharge measurement.

First, the moving unit 110 moves the conductor 2 at a predetermined speed v m/min.

Then, the conductor 2 is introduced into the insulating layer forming device 210, and an insulating coating containing, for example, a polyester imide, polyamide imide, polyimide, or the like is applied to the outer periphery of the moving conductor 2. Subsequently, the insulating layer 3 having a predetermined thickness is formed by heating (baking) the insulating coating. Then, application and baking of the insulating coating are repeatedly performed until the insulating layer 3 has an intended thickness (which ranges from 30 μm to 150 μm, for example), and thus insulated wire 1 is produced.

Next, the produced insulated wire 1 is introduced into the partial discharge measurement device 100 before it is wound up, and the above-described partial discharge measurement method is performed while the insulated wire 1 is being moved. Thus, the frequency of occurrence of partial discharge events occurring when a predetermined test voltage is applied is measured over the entire length of the insulated wire 1. Consequently, the insulated wire 1 is produced, and simultaneously a partial discharge event in the insulated wire 1 can be measured.

voltage was applied to the insulating layer. Among signals involved in partial discharge events having occurred in the insulating layer, a signal whose quantity of charge discharged was more than or equal to 100 pC was detected as a partial discharge signal by an electromagnetic-wave sensor disposed about 10 cm downstream from the electrode. Then, the frequency of occurrence of partial discharge events was measured from the result. In examples 1 to 4, a speed at which the insulated wire is moved, and a maximum value and a frequency of a sinusoidal voltage were appropriately changed as illustrated in the following table 1, and then a partial discharge measurement was made on the same insulated wire. It is noted that, in the examples 1 to 4, a sinusoidal voltage was applied so that the number of periods T of the sinusoidal voltage applied to the insulating layer is 50 periods.

TABLE 1

| | Length L of electrode [mm] | Speed v [m/min] | Sinusoidal voltage | | Number of periods T of sinusoidal voltage | Detection number of times N partial discharge event in which quantity of charge discharged is 100 pC or more has been detected | Comprehensive determination (occurrence or nonoccurrence of partial discharge event) |
|---|---|---|---|---|---|---|---|
| | | | Maximum value [Vp] | Frequency f [Hz] | | | |
| Example 1 | 150 | 20 | 800 | 111 | 50 | 0 | Nonoccurrence |
| Example 2 | 150 | 20 | 1000 | 111 | 50 | 50≤ | Occurrence |
| Example 3 | 150 | 30 | 800 | 167 | 50 | 0 | Nonoccurrence |
| Example 4 | 150 | 30 | 1000 | 167 | 50 | 50≤ | Occurrence |

It is noted that, although the case where the partial discharge measurement method is performed in an in-line manner is described in the embodiment, the present invention is not limited to this. The partial discharge measurement method according to the embodiment may be performed in an off-line manner, independently from the production of the insulated wire 1.

Furthermore, although the case where the insulating layer 3 having an intended thickness is formed by performing application and baking of the insulating coating repeatedly is described in the embodiment, the present invention is not limited to this. For example, the insulating layer 3 may be formed by moving the conductor 2 and extruding a thermoplastic resin or the like on the outer periphery of the conductor 2 with an extruder.

EXAMPLES

Next, examples of the present invention will be described.

Examples 1 to 4

First, an insulating layer having a thickness of 35 μm was formed by moving a copper wire having a conductor diameter φ of 0.80 mm, and by simultaneously applying a polyester imide resin coating to the outer periphery of the copper wire and baking the coating, and thus an insulated wire was produced. While this insulated wire was being moved at a predetermined speed, the insulated wire was brought into contact with an electrode (150 mm in length along a direction in which the insulated wire is moved) including a carbon brush, and a predetermined sinusoidal As illustrated in the example 1, in the case where a sinusoidal voltage of 800 Vp is applied, it is verified that the frequency of occurrence of partial discharge events is low over the entire length of the insulated wire, and thus it is determined in a comprehensive manner that no partial discharge events have occurred. From this, a guaranteed value of a PDIV of the insulated wire is found to be 800 Vp.

On the other hand, as illustrated in the example 2, in the case where a sinusoidal voltage of 1000 Vp is applied, it is verified that the frequency of occurrence of partial discharge events is high, and thus it is determined in a comprehensive manner that partial discharge events have occurred. From this, the guaranteed value of the PDIV of the insulated wire is found to be lower than 1000 Vp.

In the examples 3 and 4, although a speed at which the insulated wire is moved is higher than that in the examples 1 and 2, it is verified that a partial discharge measurement can be made as in the examples 1 and 2 by changing a frequency f of a sinusoidal voltage so that the number of periods T of the sinusoidal voltage is 50 periods.

Examples 5 to 8

First, an insulating layer having a thickness of 35 μm was formed by moving a copper wire having a conductor diameter θ of 0.80 mm, and by simultaneously applying a polyester imide resin coating to the outer periphery of the copper wire and baking the coating, and thus an insulated wire was produced. While this insulated wire was being moved at a predetermined speed, the insulated wire was brought into contact with an electrode (150 mm in length along a direction in which the insulated wire is moved)

including a carbon brush, and a predetermined sinusoidal voltage was applied to the insulating layer. Among signals involved in partial discharge events having occurred in the insulating layer, a signal whose quantity of charge discharged was more than or equal to 100 pC was detected as a partial discharge signal by an electromagnetic-wave sensor disposed about 10 cm downstream from the electrode. Then, the detection number of times N the partial discharge signal had been detected was measured, the detection number of times N was compared with the number of periods T of the sinusoidal voltage, and the frequency of occurrence of partial discharge events was measured on the basis of the frequency of detection. In examples 5 to 8, a maximum value and a frequency of a sinusoidal voltage were appropriately changed as illustrated in the following table 2, and then a partial discharge measurement was made on the same insulated wire. It is noted that, in the examples 5 to 8, a sinusoidal voltage was applied so that the number of periods T of the sinusoidal voltage applied to the insulating layer is 50 periods.

In a comparative example 2, an insulated wire was produced as in the comparative example 1 except that a speed at which a conductor is moved when the insulated wire is produced was changed from 20 m/min to 30 m/min.

In the comparative examples 1 and 2, PDIVs of the obtained insulated wires were measured by the following method. First, each produced insulated wire was cut into 600-mm lengths, a twisted pair wire was produced so that a twisted portion is 120 mm in length, and was subjected to terminal treatment by cutting the insulating layer away from the 10 mm-ends of the twisted pair wire, and thus a measurement sample was produced. Subsequently, ten measurement samples were prepared, and an electrode was connected to ends of the measurement samples which had been subjected to terminal treatment. Then, in an atmosphere of a temperature of 25° C. and a humidity of 50%, a sinusoidal voltage of 50 Hz was increased at 10 V/s, and a voltage at which discharge light whose quantity of charge discharged was more than or equal to 100 pC had occurred 50 times in a measurement sample was measured. Here, this

TABLE 2

| | Length L of electrode [mm] | Speed v [m/min] | Sinusoidal voltage | | Number of periods T of sinusoidal voltage | Detection number of times N partial discharge event in which quantity of charge discharged is 100 pC or more has been detected | Comprehensive determination (occurrence or nonoccurrence of partial discharge event) |
|---|---|---|---|---|---|---|---|
| | | | Maximum value [Vp] | Frequency f [Hz] | | | |
| Example 5 | 150 | 20 | 800 | 111 | 50 | 0 | Nonoccurrence |
| Example 6 | 150 | 20 | 850 | 167 | 50 | 15 | Nonoccurrence |
| Example 7 | 150 | 20 | 900 | 111 | 50 | 50≤ | Occurrence |
| Example 8 | 150 | 20 | 1000 | 111 | 50 | 50≤ | Occurrence |

As illustrated in the example 5, when an applied voltage is 800 Vp, the detection number of times N a partial discharge event has been detected is 0, and no partial discharge events have been detected. As illustrated in the example 6, when an applied voltage is increased to 850 Vp, it is verified that the detection number of times N a partial discharge event has been detected is increased to 15. However, the detection number of times N is smaller than the number of periods T, and thus it is determined that the frequency of occurrence of partial discharge events is low. As illustrated in the examples 7 and 8, when an applied voltage is increased to 900 Vp or more, it is verified that the detection number of times N is 50 or more. In this case, the detection number of times N is the number of periods T or more, and thus it is determined that the frequency of occurrence of partial discharge events is high. From the results of the examples 5 to 8, it is estimated that a guaranteed value of a PDIV of the insulated wire is in the range of 850 Vp to 900 Vp.

Comparative Examples 1 and 2

In a comparative example 1, first, an insulated wire including an insulating layer having a thickness of 35 μm was produced as in the example 1 by moving a conductor at a speed of 20 m/min, and by simultaneously applying and baking an insulating coating.

was repeated three times, and a PDIV was obtained from an average value of voltages obtained in the respective rounds.

It is verified that the PDIVs of the insulated wires obtained from measurements are 855 Vp in the comparative example 1 and 860 Vp in the comparative example 2.

As described above, in the examples 5 to 8, it is verified that, when a partial discharge measurement is made while the insulated wire is being moved, the PDIV of the insulated wire is in the range of 850 to 900 Vp. On the other hand, in the comparative examples 1 and 2 in which partial discharge measurements were made on partially-cut insulated wires without the same insulated wire being moved, it is verified that the PDIVs are respectively 855 Vp and 860 Vp. From this, it is verified that, in the examples, a partial discharge measurement can be made with the same accuracy of measurement as that in the comparative examples. In addition, in the examples, a partial discharge measurement can be made not only on part of the insulated wire but also over the entire length of it.

<Preferable Aspects of the Present Invention>

Preferable aspects of the present invention will be additionally described below.

[Appendix 1]

An aspect of the present invention provides a partial discharge measurement method including:

a moving step of moving an insulated wire including an insulating layer on a surface of the insulated wire;

a voltage applying step of bringing an electrode which is connected to a power supply into contact with the insulating layer of the insulated wire which is moving, and applying a predetermined test voltage to the insulating layer while moving the insulated wire;

a detection step of detecting, as a partial discharge signal, a signal which is more than or equal to a threshold value among signals involved in partial discharge events occurring from the insulating layer due to application of the predetermined test voltage; and a determination step of determining, based on a result in the detection step, frequency of occurrence of partial discharge events at the predetermined test voltage.

[Appendix 2]

In the partial discharge measurement method according to Appendix 1, preferably, in the voltage applying step, an alternating-current voltage is applied as the predetermined test voltage, and in a case where a frequency of the alternating-current voltage is f Hz, where a speed at which the insulated wire is moved is v m/min, and where a length of the electrode is L mm, the alternating-current voltage is applied to a contact area of the insulating layer with the electrode so that a number of periods T represented by a following equation (1) is more than or equal to 50.

$$T = \frac{60\,L}{1000\,v} f \qquad (1)$$

[Appendix 3]

In the partial discharge measurement method according to Appendix 2, preferably, in the detection step, a detection number of times N the partial discharge signal has been detected is measured, and in the determination step, the number of periods T and the detection number of times N are referred to, and it is determined that frequency of occurrence of partial discharge events is high when a relationship of T≤N is satisfied.

[Appendix 4]

In the partial discharge measurement method according to Appendix 2 or 3, preferably, in the voltage applying step, the length L of the electrode ranges from 25 mm to 200 mm inclusive.

[Appendix 5]

In the partial discharge measurement method according to Appendix 2 or 3, preferably, in the voltage applying step, the frequency f ranges from 10 Hz to 1000 Hz inclusive.

[Appendix 6]

In the partial discharge measurement method according to Appendix 2 or 3, preferably, in the moving step, the speed v ranges from 5 m/min to 40 m/min inclusive.

[Appendix 7]

In the partial discharge measurement method according to any one of Appendices 1 to 6, preferably, in the determination step, it is determined that, in the insulating layer, an area in which frequency of occurrence of partial discharge events is high is thinner in thickness of the insulating layer than an area in which frequency of occurrence of partial discharge events is low.

[Appendix 8]

Another aspect of the present invention provides a method of producing an insulated wire, the method including performing the partial discharge measurement method according to any one of Appendices 1 to 7 in an in-line manner after an insulating layer forming step of forming an insulating layer on an outer periphery of a conductor.

[Appendix 9]

Another aspect of the present invention provides a partial discharge measurement device including:

a moving unit which moves an insulated wire including an insulating layer on a surface of the insulated wire;

an electrode which is connected to a power supply generating a predetermined test voltage, is disposed so as to come into contact with the insulating layer of the insulated wire which is moving, and applies the predetermined test voltage to the insulating layer;

a detection unit which detects, as a partial discharge signal, a signal which is more than or equal to a threshold value among signals involved in partial discharge events occurring from the insulating layer due to application of the predetermined test voltage; and a determination unit which determines, based on a result in the detection unit, frequency of occurrence of partial discharge events at the predetermined test voltage.

[Appendix 10]

In the partial discharge measurement device according to Appendix 9, preferably, the power supply generates an alternating-current voltage as the predetermined test voltage, and in a case where a frequency of the alternating-current voltage is f Hz, where a speed at which the insulated wire is moved by the moving unit is v m/min, and where a length of the electrode is L mm, the electrode applies the alternating-current voltage to a contact area of the insulating layer with the electrode so that a number of periods T represented by a following equation (1) is more than or equal to 50.

$$T = \frac{60\,L}{1000\,v} f \qquad (1)$$

[Appendix 11]

In the partial discharge measurement device according to Appendix 10, preferably, the detection unit measures a detection number of times N the partial discharge signal has been detected, and the determination unit refers to the number of periods T and the detection number of times N, and determines that frequency of occurrence of partial discharge events is high when a relationship of T≤N is satisfied.

What is claimed is:

1. A partial discharge measurement method comprising:

a moving step of moving an insulated wire including an insulating layer on a surface of the insulated wire;

a voltage applying step of bringing an electrode which is connected to a power supply into contact with the insulating layer of the insulated wire which is moving, and applying a predetermined test voltage to the insulating layer while moving the insulated wire;

a detection step of detecting, as a partial discharge signal, a signal which is more than or equal to a threshold value among signals involved in partial discharge events occurring from the insulating layer due to application of the predetermined test voltage; and a determination step of determining, based on a result in the detection step, frequency of occurrence of partial discharge events at the predetermined test voltage, wherein, in the voltage applying step,
an alternating-current voltage is applied as the predetermined test voltage, and
in a case where a frequency of the alternating-current voltage is f Hz, where a speed at which the insulated wire is moved is v m/min, and where a length of the electrode is L mm, the alternating-current voltage is applied to a contact area of the insulating layer with the electrode so that a number of periods T represented by a following equation (1) is more than or equal to 50

$$T = \frac{60\,L}{1000\,v} f. \tag{1}$$

2. The partial discharge measurement method according to claim 1,
wherein, in the detection step, a detection number of times N the partial discharge signal has been detected is measured, and
wherein, in the determination step, the number of periods T and the detection number of times N are referred to, and it is determined that frequency of occurrence of partial discharge events is high when a relationship of T≤N is satisfied.

3. The partial discharge measurement method according to claim 1,
wherein, in the voltage applying step, the length L of the electrode ranges from 25 mm to 200 mm inclusive.

4. The partial discharge measurement method according to claim 1,
wherein, in the voltage applying step, the frequency f ranges from 10 Hz to 1000 Hz inclusive.

5. The partial discharge measurement method according to claim 1,
wherein, in the moving step, the speed v ranges from 5 m/min to 40 m/min inclusive.

6. The partial discharge measurement method according to claim 1,
wherein, in the determination step, it is determined that, in the insulating layer, area in which frequency of occurrence of partial discharge events is high is thinner in thickness of the insulating layer than an area in which frequency of occurrence of partial discharge events is low.

7. A method of producing an insulated wire, the method comprising
performing the partial discharge measurement method according to claim 1 in an in-line manner after an insulating layer forming step of forming an insulating layer on an outer periphery of a conductor.

8. A partial discharge measurement device comprising:
a moving unit which moves an insulated wire including an insulating layer on a surface of the insulated wire;
an electrode which is connected to a power supply generating a predetermined test voltage, is disposed so as to come into contact with the insulating layer of the insulated wire which is moving, and applies the predetermined test voltage to the insulating layer;
a detection unit which detects, as a partial signal, a signal which is more than or equal to a threshold value anion signals involved in partial discharge events occurring from the insulating layer due to application of the predetermined test voltage; and
a determination unit which determines, based on a result in the detection unit, frequency of occurrence of partial discharge events at the predetermined test voltage,
wherein the power supply generates an alternating-current voltage as the predetermined test voltage, and
wherein, in a case where a frequency of the alternating-current voltage is f Hz, where a speed at which the insulated wire is moved by the moving unit is v m/min, and where a length of the electrode is L mm, the electrode applies the alternating-current voltage to a contact area of the insulating layer with the electrode so that a number of periods T represented by a following equation (1) is more than or equal to 50

$$T = \frac{60\,L}{1000\,v} f. \tag{1}$$

9. The partial discharge measurement device according to claim 8,
wherein the detection unit measures a detection number of times N the partial discharge signal has been detected, and
wherein the determination unit refers to the number of periods T and the detection number of times N, and determines that frequency of occurrence of partial discharge events is high when a relationship of T≤N is satisfied.

* * * * *